(12) United States Patent
Yang et al.

(10) Patent No.: US 8,609,377 B2
(45) Date of Patent: Dec. 17, 2013

(54) METHOD FOR POST-EXTRACTING LOW ACYL GELLAN GUM

(75) Inventors: Baoyi Yang, Hebei (CN); Binghua Wu, Zhejiang (CN); Huaiyuan Xu, Jiangxi (CN); Zhengxue Zhu, Zhejiang (CN); Yubin Shen, Zhejiang (CN); Xuegang Wang, Zhejiang (CN); Liqiang Yang, Zhejiang (CN); Jialiang Wang, Zhejiang (CN); Wenhui Jiang, Wulanchabu (CN); Shengqiang Bao, Zhejiang (CN); Xiaolin Sheng, Zhejiang (CN); Xiaoqin Shen, Jilin (CN)

(73) Assignee: Zhejiang DSM Zhongken Biotechnology Co., Ltd., Zhejiang (CN)

( * ) Notice: Subject to any disclaimer, the term of this patent is extended or adjusted under 35 U.S.C. 154(b) by 0 days.

(21) Appl. No.: 13/142,396

(22) PCT Filed: Jun. 2, 2010

(86) PCT No.: PCT/CN2010/000782
§ 371 (c)(1),
(2), (4) Date: Jun. 27, 2011

(87) PCT Pub. No.: WO2011/003269
PCT Pub. Date: Jan. 13, 2011

(65) Prior Publication Data
US 2011/0281307 A1 Nov. 17, 2011

(30) Foreign Application Priority Data

Jul. 9, 2009 (CN) .......................... 2009 1 0158365
Jul. 9, 2009 (CN) .......................... 2009 1 0158366

(51) Int. Cl.
*C08B 37/00* (2006.01)
(52) U.S. Cl.
USPC .............. 435/101; 426/48; 426/573; 536/114
(58) Field of Classification Search
USPC ........................................ 435/101; 426/48
See application file for complete search history.

(56) References Cited

U.S. PATENT DOCUMENTS

| | | | | |
|---|---|---|---|---|
| 3,909,406 | A | * | 9/1975 | Lang .............................. 210/716 |
| 4,326,052 | A | * | 4/1982 | Kang et al. .................... 536/123 |
| 4,503,084 | A | * | 3/1985 | Baird et al. ................... 426/573 |
| 4,960,697 | A | * | 10/1990 | Johal et al. .................... 435/101 |
| 6,605,461 | B2 | | 8/2003 | Yamazaki et al. |
| 7,244,596 | B2 | * | 7/2007 | Baets et al. .................... 435/135 |
| 2008/0145505 | A1 | * | 6/2008 | Bezanson et al. ............. 426/576 |

FOREIGN PATENT DOCUMENTS

| | | | |
|---|---|---|---|
| CN | 1635133 | A | 7/2005 |
| CN | 1932026 | A | 3/2007 |
| CN | 101062957 | A | 10/2007 |
| CN | 101191138 | A | 6/2008 |
| CN | 101591399 | A | 12/2009 |
| CN | 101591400 | A | 12/2009 |
| GB | 2385330 | A * | 8/2003 |

OTHER PUBLICATIONS

Shelef et al., "Microalgae harvesting and processing: a literature review", Report, Solar Energy Research Institute, Golden Colorado, SERI/STR-231-2396, 1984.*

* cited by examiner

*Primary Examiner* — Ruth Davis
*Assistant Examiner* — Emily Cordas
(74) *Attorney, Agent, or Firm* — Drinker Biddle & Reath LLP

(57) ABSTRACT

The present invention relates to a post extraction process for preparing low acyl gellan, comprising the steps: deacylation treatment of gellan gum-containing fermentation broth, enzyme treatment, flocculation of low acyl gellan gum with divalent or polyvalent metal cations, clarification treatment of gellan gum solution, dehydration treatment of gellan gum solution, removal of divalent or polyvalent cations and decoloration, and drying and milling. Preferably, the process comprises the step of formulating a proper amount of chelating agent/acid system before the drying and milling step to chelate the added additional divalent cations added during the use of gellan gum, and at the same time to keep the pH value in a relatively stable condition. The present invention also provides the various low acyl gellan gums prepared by the above methods. The product has the following characteristics: a good appearance, a high transmittancy, and high gel strength. In particular, the chromaticity of the product is above 83%, the transmittancy is above 85%, and the gel strength is above 400 g/cm2.

80 Claims, No Drawings

METHOD FOR POST-EXTRACTING LOW ACYL GELLAN GUM

TECHNICAL FIELD OF INVENTION

The present invention relates to the field of extraction of substances from microorganism, particularly relates to a post extraction process for preparing low acyl gellan gum.

BACKGROUND

Gellan gum is one of the best thickening agents or stabilizing agents in term of performances so far, and has good gelation property. The gel of gellan gum is easy to use, has a good flavor-releasing property, has a relatively high thermal stability, is easy to melt in mouth, has a high transparence, and has a controlled gelation time and gelation temperature. And, the gelation of gellan gum is not easy to be influenced by pH. The product is stable and has a lot of texture properties with variations. The gel also has other good characteristics.

Gellan gum is a hydrophilic colloid produced by the fermentation of a bacterium, *Sphingomonas paucimobilis*, which is a strain screened and separated from the nature by a broad selection. Gellan gum has a lot of useful properties.

The molecular basic structure of the gellan gum is a main chain, constituted by the repeating units of four sugars. The basic structure of a gellan gum molecule is a main chain, constituted by the repeating four sugars units. The single sugars participating a repeated unit include D-glucose, D-glucuronic acid, D-glucose, and L-rhamnose. In the natural form of this polysaccharide, each unit has 1.5 O-acyl groups, wherein each unit has 1 O-glyceryl substituent and every two units have 1 O-acetyl substituent. The glyceryl substituent is located on Position 2 of glucose residuals linked by a bond via 3 linkages, and the acetyl substituent is located on Position 6. These acyl groups are easily removed with a base, and thereby the natural form of gellan gum can be transferred into the product in the deacylated form. In contrast with the deacylated form, the natural form of gellan gum can also be called as high acyl product.

The high acyl gellan gum contains 11~13% glyceryl groups and 4~5% acetyl groups, with the total amount of the acyl groups being in the range of 15~18% (weight percent); and, the low acyl gellan gum contains less than 1% of glyceryl groups and less than 1% of acetyl groups, with the total amount of the acyl groups being below 2%.

The acyl groups have a significant influence on the properties of the gel. The high acyl-type gellan gum can produce a gel which is soft, elastic, but does not have a brittleness while the low acyl-type gellan gum can produce a gel which is firm, does not have elasticity, but with a high brittleness.

At present, the low acyl gellan gum is broadly used in the fields, such as food industry and tissue culture media and so on. But, as to the process for preparing the low acyl gellan gum products, particularly as to the process for preparing the low acyl gellan gum products useful in these applications as mentioned above, there are only a few reports.

The low acyl, and non-clarified gellan gum product contains a part of proteins, with the amount of proteins being about 17% (weight percent). Therefore, it is not transparent. But, the low acyl and clarified gellan gum product has subjected to a filtration treatment, which removes a large part of the insoluble substances. So, the gel formed thereof is clear and transparent, having a super high transmission of light. Since the low acyl and clarified gellan gum is often used in the applications, such as food industry and so on, the tem "gellan gum", in general, means the low acyl and clarified product in most circumstances.

At present, one defect of the existing processes for producing the low acyl and clarified gellan gum lies in that there is a difficulty in the complete removal of proteins from the colloid. Thereby, the transmittancy of the product is certainly influenced, and normally it is only above 80%. At the same time, the low acyl and clarified gellan gum as produced contains some divalent metal cationic ions, which makes the gellan gum product have difficulties in dissolving, and makes the gel as formed have a slightly white color, thereby influencing the quality of the product. At the same time, the traditional process for preparing the low acyl gellan gum products uses divalent or multivalent alkali metals salts to flocculate the gellan gum product in high acyl condition, but the high acyl gellan gum has a lower sensitivity to divalent or multivalent alkali metals salts, which is largely less than the low acyl gellan gum. So, the efficiency of flocculation is not high and the yield of product is influenced.

At present, the gelling agent for tissue culture medium usually is agar. But, the impurities and the hindering elements (including the sulfur element) in agar can influence the growth of plant tissue. So, the low acyl and clarified gellan gum product is a substitute for agar, having a great promise. Because the purity of gellan gum is very high and gellan gum is produced by industrial fermentation, the product has a more stable quality in view of the product obtained by extraction of agar from algae. The gelation time for gellan gum after it has been formulated into a solution is relatively shorter than that of agar, which can save time. At the same time, the gellan gum is very stable at a high temperature, which is suitable for the cultivation of thermophile microorganisms. In the cultivation test with some plant tissues, it was found that the culture media using gellan gum can speed up the growth of plant tissues. In addition, the amount of gellan gum as used is only ⅓ of the amount of agar. The use of gellan gum can fight against the contamination of mildews. In the replanting process, the cleaning procedure for gellan gum is easy. Further, the use of gellan gum can conduce to the easy observation of the growth of roots and the growth of tissues because the gel formed from gellan gum has a superior transmission of light. Therefore, the low acyl gellan gum also has a broad application promise in the tissue culture medium.

At present, although the food-level low acyl gellan gum produced by industry can be used in the products for tissue culture, the food-level gellan gum produced domestically has a lot of problems in the application for preparing culture medium, if compared with the low acyl gellan gum under the trade name GELZAN™ CM type, provided by CP KELCO Inc., USA and the low acyl gellan gum under the trade name PHYTAGEL Model, provided by SIGMA Corporation. The details are listed as follows:

1. The food-level low acyl gellan gum has a poor solubility and a poor dispensability, is easy to associate, and has a hydration temperature of above 80° C. But, the gellan gum for culture medium produced by oversea companies has a good dispensability and a hydration temperature of about 60° C.

2. The general food-level gellan gum needs to be strictly treated with a specific procedure during the usage process, wherein the specific procedure has the following order of firstly dissolving the colloid and then adding the metal ions into the solution. If the gellan gum powder and the metal salts were firstly mixed, and the mixture of gellan gum power and metal salts were then dissolved, it would lead to a difficulty in dissolving process and would produce a lot of milk-white flocculent. But, the gellan gum provided by oversea companies does not have this problem.

3. The general food-level gellan gum has the gel strength of above 900 g/cm2. But, the gellan gum for culture medium provided by the oversea companies has the gel strength of 400∞600 g/cm2. At the same time, the general food-level gellan gum has a light transmission of about 85% while the gellan gum product for culture medium provided by the oversea companies has a light transmission of above 90%.

SUMMARY OF INVENTION

In view of the various defects existing in the processes for preparing the low acyl gellan gum products as mentioned above, one aim of the present invention is to provide a novel method for producing a low acyl gellan gum. Further, the other aims of the present invention are to provide a novel method for producing a low acyl and clarified gellan gum, and a method for producing a low acyl and clarified gellan gum suitable for use in the preparation of a tissue culture medium.

The present invention relates to a process for extracting a low acyl and clarified gellan gum, comprising the steps of a deacylation treatment of the fermentation broth containing gellan gum, a treatment with enzyme, a flocculation of the low acyl gellan gum with divalent or multivalent metal cationic ions, a clarification treatment of gellan gum solution, a dehydration treatment of gellan gum solution, a removal of the divalent or multivalent metal cationic ions, a decoloration treatment, and a drying and milling treatment. Preferably, a proper amount of chelating agent/acid system calculated by mass may be formulated before the step of drying and milling so that the additional divalent cationic ions added during the usage process of gellan gum may be chelated and the pH value is kept in a relative stabilization status. The detailed steps include:

The deacylation treatment of the fermentation broth

The temperature of the fermentation broth is raised to 80~90° C., and an anti-oxidant agent is added into the fermentation broth, and at the same time, a base is added to adjust the pH value so that the deacylation occurs;

The enzyme treatment of the fermentation broth;

Into the fermentation broth obtained in Step (1), different enzyme preparations are added so that the insoluble impurities and bacterial debris are eliminated from the fermentation broth as much as possible. In particular, another enzyme is added and kept in a second specific temperature for a second enzyme hydrolysis after the first enzyme hydrolysis has finished by adding a first enzyme preparation and keeping the mixture at a first specific temperature, and the other enzyme preparations may be added in the same one-by-one way.

(3) The flocculation of the fermentation broth

Into the fermentation broth obtained in Step (2), a water-soluble alkali metal is added to flocculate, and then the pH value is adjusted into the basic condition, and then a solid-liquid separation is conducted so that the most part of the water and pigments in the fermentation broth is removed, thereby, the concentrated gellan gum raw product is obtained;

(4) The clarification treatment of gellan gum

The gellan gum raw product obtained in Step (3) is subjected to a clarification treatment so that the clarified, low acyl gellan gum solution is obtained;

(5) The dehydration treatment of the deacylated gellan gum solution

Into the deacylated and clarified gellan gum solution obtained in Step (4), the alkali metal ions are added to form a gel and the gel is pressed to dehydrate the water;

(6) The removal of divalent or multivalent cations and the decoloration treatment Cut the gellan gum obtained in Step (5) into fine grains, remove a large part of the divalent or multivalent cations by ion exchange chromatography or chelating chromatography; slightly press and dry the gellan gum, and then, the gellan gum is immersed in a lower alcohol under agitation, then a filtration is conducted to reach the effect of a complete decoloration;

(7) Drying and Milling;

Dry and mill the solid material of gellan gum obtained in Step (6) to produce the low acyl and clarified gellan gum product which has a high transparance.

As a preferable embodiment, there are the following steps between Step (6) and (7):

(6') Introduction of proper amount of chelating agent/acid system

A proper amount of chelating agent/acid system is formulated into the gellan gum obtained in Step (6) to chelate the possibly additionally added divalent cations during the use of gellan gum, and to keep the pH value relatively stabilized. Mix the mixture by agitation until the even condition is reached.

More particularly, the method includes:

1. Deacylation treatment of fermentation broth

Raise the temperature of the fermentation broth up to a temperature in the range of 85~90° C., and add a suitable amount of antioxidant into the fermentation broth. At the same time, add a base to adjust the pH into the range of pH 9.5~11. Then, a slow agitation is subjected to the fermentation broth for 10~15 minutes. This procedure will remove the glyceryl groups and the acetyl groups on the main chains of gellan gum molecules. After that, an acid is added to adjust the pH value to the neutral condition, and the temperature is reduced to a temperature below 40° C.

2. Enzyme treatment of fermentation broth

Into the fermentation broth obtained in Step (1), cellulase, lysozyme and protease, at different concentrations, dispersed in a little amount of water, are respectively added and kept for different times. The protease is a neutral protease or an alkaline protease.

3. Flocculation treatment of feimentation broth

Cool down the material obtained in Step (2) at a temperature below 35° C., and add a divalent or multivalent alkaline metal salt into it to flocculate the low acyl gellan gum. Then, add a base to adjust the pH and conduct a solid-liquid separation via filtration or pressing.

4. Clarification treatment of gellan gum

Break up the material obtained in Step (3) into the broken material and dissolve the broken material with deionized water in the amount of 10~20 times of the broken material in volume. Then, an acid is added to adjust back the pH value to the neutral condition. The temperature is raised up to 85~90° C. A complete agitation is given to reach a full dissolution. 9A filtration is conducted, via a plate-frame device or a chamber-type pressing device, or high speed centrifugation or a microporous filter membrane. The deacylated gellan gum obtained in Step (3) is clarified, with the temperature for clarification being a temperature above 65° C. to prevent the formation of gel from the solution. The clarified solution as obtained has a light transmission of more than 92%.

5. Dehydration treatment of the deacylated gellan gum solution

Into the deacylated and clarified gellan gum obtained in Step (4), a proper amount of metal cations salts are added to form a gel and then the gel is dehydrated by pressing. So, the colloid curds or colloid sheets of the low acyl and clarified gellan gum are obtained with the water content being about 80%.

6. Removal of divalent or multivalent cations and decoloration treatment

Cut the low acyl gellan gum with the water content of about 80% obtained in Step (5) into small grains. Then, the small grains are dropped into water in the amount of 3~5 times of the small grains in mass which has been treated with a proper amount of monovalent alkali metal salts. The water immerses the small grains for a time, with an agitation at high speed. Later, the colloid in divalent cation form is converted into monovalent cation form vie ion exchange chromatography. Or, the small grains are dropped into 3~5 times of water in mass of the small grains which has been treated with a proper amount of chelating agent. Then, the water immerses the small grains for a time, with an agitation at high speed to remove most of the divalent or multivalent cations. The treated gellan gum solution is pressed to lose the water. Then, it is immersed into 2 times of lower alcohol solution in mass for a time under an agitation at high speed. After that, a filtration is conducted to reach the effect of completely removing pigments.

7. Drying and milling;

Dry the product obtained in Step (6) at the temperature of 75~80° C., and mill it so that 95% of it can pass a sieve of 80 meshes. So, the low acyl and clarified gellan gum product is obtained.

As a preferable embodiment, there is the following step between Steps (6) and (7) as described below:

(6'). Formulating a proper amount of chelating agent/acid system

Into the gellan gum obtained in Step (6), a proper amount of chelating agent/acid system is formulated, in order to chelate the divalent cations which may be additionally added during the use of gellan gum, and to keep the pH value in a relatively stable condition. At this moment, the water content in the gellan gum is about 80%. The chelating agent/acid system is mixed with the gellan gum and forms an evenly-mixed composition by an agitation. In the chelating agent/acid system, the chelating agent and the acid may be added after mixing, or may be added in turns.

The specific processing conditions for each step of the present invention are:

In Step 1, the antioxidant may be, but not limited to, one or more of ascorbic acid, sodium erythorbate, sodium pyrosulfite, potassium pyrosulfite, potassium bisulfate, and cysteine. The concentration of the antioxidant added, preferably, is 100~300 ppm; more preferably, is 150~250 ppm (calculated based on the fermentation broth).

In Step 1, the base added for adjustment of the pH, is one or more selected from the group consisting of NaOH, KOH, Na2CO3, and K2CO3, but not limited to the above listing. More preferably, it is NaOH or KOH. Most preferably, it is NaOH.

In Step 1, the pH value is adjusted to the range of 9.5~11 with a base. More preferably, the pH value is about 10.

In Step 1, the base for adjusting the pH is firstly formulated into a 10% solution.

In Step 1, the temperature is maintained in the range of 85~90° C. More preferably, the temperature is maintained in the range of 86~88° C.

In Step 1, the temperature is kept as indicated for a time period of 10~15 minutes. More preferably, the temperature is kept as indicated for about 10 minutes.

In Step 1, the acid for adjusting the pH may be an inorganic acid, or it may be an organic acid. According to the invention, the inorganic acid comprises, but not limited to, one or more of hydrochloric acid, sulfuric acid, and phosphoric acid. The organic acid may be, but not limited to formic acid, acetic acid, citric acid, malic acid or tartaric acid. In the practice of the production, it is preferable to use the inorganic acid as the said acid. More preferably, hydrochloric acid may be used. The amount of acid as used is the amount that can adjust the pH of the system of the fermentation broth to about 7.

In Step 1, the acid for adjusting pH should be firstly formulated into a 10% solution.

In Step 2, the zymolysis conditions respectively are described as follows. For cellulase, the concentration is preferably 500~2000 ppm, more preferably 1000~1500 ppm; and the zymolysis time is preferably 4 to 8 hours, more preferably 5 to 6 hours; and the zymolysis temperature is preferably 40~50° C., more preferably 43~45° C. For lysozyme, the concentration is preferably 50~300 ppm, more preferably 100~200 ppm; the zymolysis time is preferably 2 to 4 hours, more preferably 2.5 to 3.5 hours; and the zymolysis temperature is preferably 30~40° C., more preferably 35~37° C. For protease, the concentration is preferably 100~1000 ppm, more preferably 300~500 ppm (calculated on the basis of the fermentation broth); and the zymolysis time is preferably 1 to 5 hours, more preferably 2 to 3 hours; and the zymolysis temperature is preferably 30~40° C., more preferably 30~35° C. And the protease may be a neutral protease or an alkaline protease.

In Step 3, the water-soluble alkali metal salt as used includes, but not limited to a water-soluble salt of magnesium, calcium, barium, zincum, and aluminium, or a combination thereof.

In Step 3, the amount of the water-soluble alkali metal salt as added account for preferably 0.1%~0.5% of the fermentation broth in mass, more preferably 0.3%~0.4% of the fermentation broth in mass.

In Step 3, the base as used includes, but not limited to: one or more of KOH, NaOH, Na2CO3, NaHCO3, and. Na3PO4.

In Step 3, the device for the solid-liquid separation as used may be selected from, but not limited to, a chamber-type polypropylene plate-and-frame filter press or a sack press. It is preferable to use a chamber-type polypropylene plate-and-frame filter press.

In Step 4, the length of the fibers of gellan gum after breaking up should not be more than 10 cm, and the water content in the fibers is about 80%.

In Step 4, the broken gellan gum fibers are dissolved with deionized water in the amount of 10 to 20 times of the broken gellan gum, more preferably with deionized water in the amount of 15~20 times of the broken gellan gum. Heat the solution and make the temperature of the solution up to 80~95° C., more preferably up to 85~90° C.

In Step 4, the clarification device may be selected from, but not limited to, a plate-and-frame type filter press or a chamber-type filter press, high speed configuration, or microporous membrane filtration. Preferably, the clarification device may be a plate-and-frame filter press or a chamber-type filter press.

In Step 4, the temperature for clarification treatment should be above 65° C. to prevent from the formation of a gel from the solution. More preferably, the temperature is about 75° C.

In Step 5, the metal salt added for the formation of gel includes, but not limited to, a soluble monovalent alkali metal salt (one or more of potassium chloride, sodium chloride, potassium sulfate, and sodium sulfate), a divalent alkali metal salt (calcium chloride, magnesium chloride) and a multivalent alkali metal salt (ferric chloride), and so on. The metal salt may be a combination of the above alkali metal salts. Preferably, the metal salt may be monovalent or divalent alkali metal salts. In consideration of the cost factor, it is more preferable to use divalent alkali metal salts.

In Step 5, the monovalent alkali metal salt added for the formation of gel is added at the amount of 0.8~1.2% (weight percent) of the clarified gel solution, and the divalent metal salt is added at the amount of 0.05~0.1% (weight percent) of the clarified gel solution.

In Step 5, the soluble metal salt added for the formation of gel should be formulated into a solution at the concentration of 30%.

In Step 5, the device for solid-liquid separation may be selected from, but not limited to, a chamber-type polypropylene plate-and-frame filter press or a sack press. Preferably, the device may be a chamber-type polypropylene plate-and-frame filter press.

In Step 6, a cutting machine is used to cut the low acyl gellan gum into column-like small grains, with the diameter of the grains being less than 3 mm, and the length of the grains being less than 12 mm.

In Step 6, the monovalent metal cation includes, but not limited to, a soluble monovalent alkali metal salt (one or more of potassium chloride, sodium chloride, potassium sulfate, and sodium sulfate). The amount is preferably that amount which makes the concentration in the solution reach 5000~10000 ppm. More preferably, the amount is 6000~8000 ppm.

In Step 6, the chelating agent according to the present invention may be, but not limited to, one or more of sodium citrate, tripotassium citrate, sodium hexametaphosphate, potassium hexametaphosphate, sodium pyrophosphate, and potassium tripolyphosphate. The preferable chelating agent for use is sodium citrate or sodium hexametaphosphate. The more preferable chelating agent is sodium citrate. The amount of chelating agent added is preferably the amount that makes the concentration in the solution be 1000~10000 ppm, more preferably 5000~8000 ppm.

In Step 6, the dehydration pressing device in use is a sack press.

In Step 6, the lower alcohol in use may be one or more of ethanol, isopropanol, and n-butanol. Preferably, the lower alcohol is ethanol or isopropanol. More preferably, the lower alcohol is isopropanol. The amount as used is preferably 2~4 times of the wet weight of the gellan gum grains, and more preferably 2.5~3.5 times of the wet weight of the gellan gum grains.

In Step 6', the chelating agent in use includes, but not limited to, one or more of sodium citrate, tripotassium citrate, sodium hexametaphosphate, potassium hexametaphosphate, sodium pyrophosphate, potassium tripolyphosphate. In the practice of production, preferably, the chelating agent in use is the chelating agent, i.e., salts of phosphoric acid. More preferably, the chelating agent is sodium hexametaphosphate.

In Step 6', the acid in use may be an inorganic acid or an organic acid. The inorganic acid may be, but not limited to, one or more of hydrochloric acid, sulfuric acid or phosphoric acid. The organic acid may be, but not limited to, one of more of formic acid, acetic acid, citric acid, malic acid or tartaric acid. In the practice of production, the acid in use is preferably an organic acid, more preferably citric acid.

In Step 6', the chelating agent is used at the amount accounting for 9~10% (mass percent) of the final dried product. The acid is used at the amount accounting for 0.5~1% (mass percent) of the final dried product.

In Step 7, the drying device in use may be, but not limited to, a vacuum drying device or a boiling dryer. The temperature for drying is controlled in the range of 75~80° C., and the time for drying is controlled in the range of 1 to 1.5 hours.

The present invention is illustrated by the following examples, which are provided for a better understanding of the present invention. The examples are not limited, only to illustrate the present invention, not to limit the scope of the present invention.

(I) Extraction of the Low Acyl and Clarified Gellan Gum

Example 1

A. Deacylation Treatment of Fermentation Broth

In the flocculation tank, 10 m3 of gellan gum-containing fermentation broth is heated to the temperature of 90° C. Then, under agitation, ascorbic acid is added until the concentration of ascorbic acid reaches 150 ppm. And, further, KOH solution having the concentration of 10% is added to adjust the pH to 10.0. On the condition that the temperature is maintained at 90° C. and the agitation is further slowly conducted for 10 minutes. After this, hydrochloric acid having the concentration of 10% is added to adjust the pH back to 7.0, and the obtained solution is subjected to the next step.

B. Enzyme treatment of fermentation broth

Under agitation, 15 kg of cellulase is added and the temperature is maintained at 45° C. A slow agitation is conducted for 5.5 hours. After this, 2 kg of lysozyme is added and the temperature is 35° C. A slow agitation is continued for 3 hours. Then, 4 kg of neutral protease is added and the temperature is 33° C. A slow agitation is continued for 2.5 hours.

C. Flocculation of fermentation broth

Into the above liquid feed, 30 kg of magnesium chloride is slowly added and an agitation is lasted for 20 minutes. Then, 20 kg of sodium hydroxide is added and an agitation is conducted for 10 minutes. After this, the feed is pumped into a chamber-type plate-and-frame filter press to filter. The filtrate is discharged into a wastewater treatment station, and the so-obtained 950 kg wet cake is ready to the later use.

D. Clarification treatment of gellan gum

The cake obtained in C is firstly broken up to short fibers with a beater. Then, deionized water at the amount of 15 times of the weight of the fibers is added and the solution is heated until the temperature reaches 90° C. Into the heated solution, a proper amount of diatomite is added and evenly dispersed by agitation. The temperature is controlled at around 85° C., and the gellan gum solution so-obtained is cyclically filtered with a chamber-type polypropylene plate-and-frame filter press pre-coated with the diatomite filter aid until the clarified gellan gum solution so obtained reaches a light transmittancy of more than 92% determined with a spectrophotometer. The resultant clarified solution is fed to a gel tank.

E. Dehydration treatment of the deacetylated gellan gum solution

The temperature of the gellan gum solution obtained in D needs to be kept at a temperature of above 65° C. to prevent from the formation of a gel. Then, 400 L of potassium chloride solution having the concentration of 30% is added into the gellan gum solution, and a slow agitation is performed for 5 minutes. After that, the gellan gum solution is forcedly cooled to a temperature below 50° C. A hard and brittle gel forms, and the colloid is pressed with a chamber-type polypropylene plate-and-frame filter press, to produce pieces or curds of gellan gum having a water content of about 80%, with the total weight of 500 kg.

F. Chelating and decoloration treatment

The pieces or curds of the gellan gum obtained in E are cut into fine column-shaped grains by a cutter. The grains have a diameter of less than 3 mm, and a length of less than 12 mm. The gellan gum grains are plunged into deionized water in the amount of 3 times of the gellan gum grains calculated based on the mass. At the same time, potassium hexametaphosphate is added until the concentration of potassium hex ametaphosphate reaches 5000 ppm. The mixture solution is slowly agitated for 10 minutes, and then filtered with filter cloth. The filter residue is immersed in ethanol solution in the amount of 2.5 times of the weight of filter residue, and a quick agitation is conducted for 30 minutes. The ethanol solution is removed with a sack press. 495 kg of wet gellan gum, in the form of loose grains, is obtained.

G. Drying and milling

The product obtained in F passes a boiling dryer. At the temperature of 75° C., the drying process is performed. Then, the dried product is milled until 95% of it passes a sieve of 80 meshes. 100 kg of low acyl and clarified gellan gum product is obtained.

Example 2

A. Deacetylation treatment of fermentation broth

In the flocculation tank, 10 m3 of gellan gum-containing fermentation broth is heated and the temperature of the fermentation broth reaches 90° C. Under agitation, sodium erythorbate is added until the concentration of sodium erythorbate reaches 200 ppm. And then, NaOH solution having the concentration of 10% is added to adjust pH to 10.0. At the temperature of 90° C., a slow agitation is continued for 10 minutes. After that, acetic acid solution having the concentration of 10% is added to adjust pH back to 7.0. The solution as obtained is subjected to the next step.

B. Enzyme treatment of fermentation broth

Under agitation, 15 kg of cellulase is added and the temperature is kept at 43° C., and a slow agitation is conducted for 5 hours. Then, 2 kg of lysozyme is further added and the temperature is kept at 33° C., and a slow agitation is conducted for 3 hours. And, later, 4 kg of alkaline protease and the temperature is kept at 35° C., and a slow agitation is conducted for 3 hours.

C. Flocculation of fermentation broth

Into the above feed, 35 kg of calcium chloride is slowly added, and an agitation is continued for 20 minutes. And then, 20 kg of potassium hydroxide is added and the agitation is kept for 10 minutes. The feed is pumped into a chamber-type plate-and-frame filter press to filter. The filtrate is exited into a wastewater treatment station, and 950 kg of a wet cake is obtained for later use.

D. Clarification treatment of gellan gum

The cake obtained in C is firstly broken up into short fibers with a beater. And, deionized water in the amount of 15 times of the weight of the cake is added. The solution is heated so that the temperature of the solution is raised up to 90° C. The gellan gum solution is cyclically filtered with a micro-porous membrane until the clear gellan gum solution obtained reaches the transmittancy of more than 92%, measured by a spectrophotometer. The clarified solution is fed into a gel tank.

E. Dehydration treatment of the deacetylated gellan gum solution

The temperature of the clarified gellan gum solution obtained in D is kept at a temperature of above 65° C. to prevent from the formation of gel. Then, into the solution, 400 L of sodium chloride solution having the concentration of 30% is added and a slow agitation is conducted for 5 minutes. After this, the solution is forcedly cooled to a temperature below 50° C. The colloid as formed is hard and brittle, which is pressed with a chamber-type polypropylene plate-and-frame filter press. Then, 500 kg of gellan gum in pieces or curds with the water content of about 80% is obtained.

F. Chelating and decoloration treatment

The pieces or curds of gellan gum obtained in E are cut into small column-shaped grains. The diameter of the grains is less than 3 mm, and the length of the grains is less than 12 mm. The grains of gellan gum are emptied into deionized water of the amount of 3 times of the weight of the gellan gum grains. At the same time, sodium citrate is added until the concentration of sodium citrate reaches 5000 ppm. Then, a slow agitation is conducted for 10 minutes, and a filtration is done with filter cloth. The filter residue is further immersed into isopropanol solution of 2.5 times of the weight of the filter residue, and a quick agitation is conducted for 30 minutes. The alcohol solution is removed by a sack press, and thereby, 495 kg of loose grains of wet gellan gum are obtained.

G. Drying and milling

The product obtained in F passes a boiling dryer and is dried at the temperature of 75° C. The dried product is milled to make 95% of it pass a sieve of 80 meshes. Thereby, 100 kg of low acyl and clarified gellan gum product is obtained.

Example 3

A. Deacetylation treatment of fermentation broth

In a flocculation tank, 10 m3 of gellan gum-containing fermentation broth is added and heated to the temperature of 90° C. And under agitation, potassium pyrosulfite is added until the concentration of potassium pyrosulfite reaches 250 ppm. Then, KOH solution having the concentration of 10% is added to adjust the pH to 10.0. In the condition that the temperature is 90° C., a slow agitation is conducted for 10 minutes. And then, citric acid with the concentration of 10% is added to adjust back pH to 7.0. The solution as obtained is used for next step.

B. Enzyme treatment of fermentation broth

Under agitation, 15 kg of cellulase is added and the temperature is kept at 43° C. A slow agitation is conducted for 5 hours. Then, 2 kg of lysozyme is further added and the temperature is kept at 33° C. A slow agitation is conducted for 3 hours. Then, 4 kg of alkaline protease is further added and the temperature is kept at 35° C. A slow agitation is conducted for 3 hours.

C. Flocculation of fermentation broth

Into the above feed liquid, 35 kg of zincum chloride is slowly added, and the agitation is continued for 20 minutes. Then, 20 kg of sodium carbonate is slowly added and a further agitation is continued for 10 minutes. The feed is pumped into a chamber-type plate-and-frame filter press to filter. The filtrate is exited to a wastewater treatment station. The wet cake with the weight of 950 kg as obtained is kept for later use.

D. Clarification treatment of gellan gum

The cake obtained in C is firstly broken up into short fibers with a beater. Then, deionized water with the amount of 15 times of the weight of the short fibers is added. The solution is heated so that the temperature is raised up to 90° C. Into the solution, a suitable amount of diatomite is added and dispersed evenly by agitation. The temperature is controlled at 85° C., and a chamber-type polypropylene plate-and-frame filter press having the pre-coating of filtration aiding agent for diatomite cyclically filters the gellan gum solution, until the clarified gellan gum solution as obtained has a transmittancy of more than 92% measured by a spectrophotometer. The clarified solution is pumped into the gel tank.

E. Dehydration treatment of the deacetylated gellan gum solution

The temperature of the gellan gum solution obtained in D needs to be kept at a temperature of above 65° C. to prevent from the formation of gel. Then, into the solution, 25 L of calcium chloride solution having the concentration of 30% is added, and a slow agitation is kept for 5 minutes. Then, a forced cooling is conducted so that the temperature is reduced to a temperature below 50° C. The colloid of the firm and brittle gel as formed is pressed with a chamber-type polypropylene plate-and-frame filter press, and produces 500 kg of gellan gum sheets or curds, having the water content of about 80%.

F. Chelating and decoloration treatment

The gellan gum sheets or curds obtained in E are cut into column-shaped grains with a cutter. The diameter of the grains is less than 3 mm, and the length of the grains is less than 12 mm. The gellan gum grains are plunged into deionized water of 3 times of the gellan gum grains in mass, and at the same time, potassium tripolyphosphate is added so that the concentration of potassium tripolyphosphate reaches 5000 ppm. A slow agitation is conducted for 10 minutes. After this, the solution is filtered with a filter cloth. The filter residue is further immersed with ethanol solution in the amount of 2.5 times of the filter residue in weight, and a quick agitation is conducted for 30 minutes. The ethanol solution is removed with a sack press. A total of 495 kg of gellan gum in wet and loose grains is obtained.

G. Drying and milling

The product obtained in F passes a boiling dryer and is dried at the temperature of 75° C. Then, the dried product is milled so that 95% of it can pass the sieve of 80 meshes. 100 kg of low acyl and clarified gellan gum is obtained.

In view of the existing post extraction processes for preparing low acyl gellan, using the above process has the following advantages:

1. Because the deacetylation treatment of the fermentation broth makes use of the temperature formed during the sterilization with high temperature, the process is simplified, and the overall process according to the invention has a lower energy consumption compared to the existing processes.

2. Because the product is subjected to a deacetylation treatment before the flocculation treatment, the flocculation of low acyl gellan gum with divalent or multivalent metal cations shows a higher efficiency, which increases the yield.

3. The appearance of product is largely improved, reaching the advance level in this country and outside this country. The appearance of product is good, the transmittancy is high, and the gel strength of the product is high. In details, the product shows a chromaticity of above 83%, a transmittancy of above 85%, and gel strength of above 1000 g/cm2.

4. Most of divalent metal cations are removed with the chelating process during the later phrase so that the phenomenon that the formed gel has a slightly whitening color disappears. This improves the quality of product.

(II) The Preparation of Low Acyl and Clarified Gellan Gum Suitable for Use in Tissue Culture Medium Example 4

A. Deacylation treatment of fermentation broth

In a flocculation tank, 10 m3 of gellan gum-containing fermentation broth is added and heated so that the temperature of the gellan gum-containing fermentation broth is raised to 90° C. Under agitation, ascorbic acid is added until its concentration reaches 150 ppm. Then, KOH having the 10% concentration is added to adjust the pH to 10.0. And, at the temperature of 90° C., a slow agitation is conducted for 10 minutes. After this, hydrochloric acid having the concentration of 10% is added to adjust back the pH to 7.0. The solution as obtained is subjected to the next step.

B. Enzyme treatment of fermentation broth

Under agitation, 15 kg cellulase is added and the temperature kept at 45° C. A slow agitation is conducted for 5.5 hours. Then, 2 kg lysozyme is further added and the temperature kept at 35° C. A slow agitation is conducted for 3 hours. Then, 4 kg neutral protease is further added and the temperature kept at 33° C. A slow agitation is conducted for 2.5 hours.

C. Flocculation of fermentation broth

Into the above feed liquid, 30 kg of magnesium chloride is slowly added and an agitation is kept for 20 minutes. Then, 20 kg of sodium hydroxide is added and the agitation is kept for additional 10 minutes. The feed liquid is pumped into a chamber-type plate-and-frame filter press to filter. The filtrate is exited into a wastewater treatment station. The 950 kg of wet cake as obtained is obtained and ready for later use.

D. Clarification treatment of gellan gum

The cake obtained in C is firstly broken up with a beater into short fibers, which are immersed into deionized water having the amount of 15 times of the short fibers in weight.

Then, the solution is heated to 90° C. Into the solution, a suitable amount of diatomite is added and an agitation is used to disperse the added diatomite evenly. The temperature is controlled at 85° C. and the gellan gum solution is filtered with a chamber-type polypropylene plate-and-frame filter press having a pre-coating of filtering aid for diatomite in a cycle format. The cycle filtration is conducted until the clarified gellan gum solution has a transmittancy of more than 92% detected with a spectrophotometer. The clarified solution is pumped into a gel tank.

E. Dehydration treatment of the deacylated gellan gum solution

The temperature of the gellan gum solution obtained in D should be kept at a temperature above 65° C. to prevent from the formation of a gel. Then, into the solution, 400 L of potassium chloride solution with the concentration of 30% is added and a slow agitation is conducted for 5 minutes. After this, the temperature of the solution is forcedly reduced to a temperature of below 50° C. The colloid of the hard and brittle gel as formed is pressed with a chamber-type polypropylene plate-and-frame filter press. The gellan gum product, in form of gum sheets or curds, having a water content of about 80%, with a total weight of 500 kg, is obtained.

F. Ion exchange and decoloration treatment

The gellan gum sheets or curds obtained in E are cut into column-shaped grains with a cutter. The diameter of the grains is less than 3 mm, and the length of the grains is less than 12 mm. The gellan gum grains are plunged into deionized water of the amount of 3 times of the mass of the gellan gum grains. At the same time, potassium chloride solution is added until the concentration of potassium chloride reaches 5000 ppm, and a slow agitation is conducted for 10 minutes. After this, the solution is filtered with a filter cloth. The filter residue is further immersed with ethanol solution of the amount of 2.5 times of the weight of the filter residue and a quick agitation is conducted for 30 minutes. And then, a sack press is used to remove the ethanol solution. Finally, 495 kg of wet and loose gellan gum grains are obtained.

G. Formulation of a proper amount of chelating agent/acid system

Into the gellan gum obtained in F, 10 kg of sodium hexametaphosphate is added and then 1 kg of citric acid added. All the materials are mixed evenly by agitation.

H. Drying and milling

The product obtained in G passes a boiling dryer and is dried at the temperature of 75° C. Then, the dried product is milled so that 95% of the product can pass a sieve of 80 meshes. The low acyl and clarified gellan gum product, a total of 110 kg, is obtained.

Example 5

A. Deacylation treatment of fermentation broth

Into a flocculation tank, 10 m3 of gellan gum-containing fermentation broth is added and heated to the temperature of 90° C. Under agitation, sodium erythorbate is added until the concentration thereof reaches 200 ppm. Then, 10% NaOH solution is added to adjust the pH to 10.0. The temperature is kept at 90° C., and the slow agitation is continued for 10 minutes. After this, 10% acetic acid solution is added to adjust back the pH to 7.0. The solution as obtained is subjected to the next step.

B. Enzyme treatment of fermentation broth

Under agitation, 15 kg cellulase is added into the fermentation broth treated in A and the temperature is kept at 43° C. and a slow agitation is conducted for 5 hours. Then, 2 kg lysozyme is added and the temperature is kept at 33° C. and a slow agitation is conducted for 3 hours. After this, 4 kg alkaline protease is added and the temperature is kept at 35° C. and a slow agitation is conducted for 3 hours.

C. Flocculation of fermentation broth

Into the above feed liquid, the salt, i.e., calcium chloride, 35 kg, is slowly added. And a agitation is lasted for 20 minutes. Then, potassium hydroxide, 20 kg, is added. The agitation is kept for 10 minutes. The feed is pumped into a chamber-type plate-and-frame filter press to filter. The filtrate liquid is exited into a wastewater treatment station. And, 950 kg of wet cake is ready for later use.

D. Clarification treatment of gellan gum

The cake obtained in C is firstly broken up with a beater into short fibers. Then, deionized water is added, at the amount of 15 times of the short fibers in weight. The solution as obtained is heated so that the temperature of the solution reaches 90° C. Using a microporous filter membrane, the gellan gum solution is cyclically filtered until a clarified gellan gum solution is obtained, which has a transmittancy of more than 92% measured with a spectrophotometer. The clarified solution is pumped into a gel tank.

E. Dehydration treatment of the deacylated gellan gum solution

The temperature of the gellan gum solution obtained in D should be kept at a temperature over 65° C. to prevent from the formation of a gel. Then, into the solution, 400 L of sodium chloride solution having the concentration of 30% is added and the slow agitation is conducted for 5 minutes. After this, a forced cooling is conducted so that the temperature reduces to a temperature of below 50° C. The colloid of the hard and brittle gel as formed is pressed with a chamber-type polypropylene plate-and-frame filter press to produce 500 kg of sheets or curds of gellan gum having a water content of about 80%.

F. Ion exchange and decoloration treatment

The gellan gum sheets or curds obtained in E are cut into column-shaped grains with a cutter. The diameter of the grains is less than 3 mm, and the length of the grains is less than 12 mm. The gellan gum grains are plunged into deionized water of the amount of 3 times of the gellan gum grains in mass. And at the same time, sodium chloride is added until the concentration of sodium chloride reaches 7000 ppm. A slow agitation is conducted for 10 minutes. Then, a filtration is performed with a filter cloth. The filter residue is immersed with isopropanol solution of the amount of 2.5 times of the weight of the filter residue in weight, and a quick agitation is conducted for 30 minutes. A sack press is used to remove the isopropanol solution. 495 kg of wet gellan gum grain in loose condition is obtained.

G. Formulating a proper amount of chelating agent/acid system

Into the gellan gum obtained in F, 10.5 kg of sodium citrate is added and 1 kg of malic acid added. And the mixture is mixed evenly.

H. Drying and milling

The product obtained in G passes a boiling dryer, and is dried at the temperature of 75° C. The dried product is milled so that 95% of it passes a sieve of 80 meshes. 110 kg of low acyl, clarified gellan gum product is obtained.

Example 6

A. Deacetylation treatment of fermentation broth

In a flocculation tank, 10 m3 of gellan gum-containing fermentation broth is added and heated to the temperature of 90° C. With agitation, potassium pyrosulfite is added into the fermentation broth until the concentration of the potassium pyrosulfite reaches 250 ppm. And then, KOH solution with the concentration of 10% is added to adjust the pH to 10.0. At the condition that the temperature is 90° C., a slow agitation is conducted for 10 minutes. After this, citric acid with the concentration being 10% is added to adjust back the pH to 7.0. The solution as obtained is subjected to the next step.

B. Enzyme treatment of fermentation broth

Under agitation, 15 kg of cellulase is added and the temperature kept at 43° C., and a slow agitation is conducted for 5 hours. Then, 2 kg of lysozyme is further added and the temperature kept at 33° C., and a slow agitation is conducted for 3 hours. After this, 4 kg of alkaline protease is added and the temperature kept at 35° C., and a slow agitation is conducted for 3 hours.

C. Flocculation of fermentation broth

Into the above feed liquid, 35 kg of zincum chloride is slowly added and the agitation is kept for 20 minutes. Then, 20 kg of sodium carbonate is added and the agitation is kept for 10 minutes. The feed is pumped into a chamber-type plate-and-frame filter press to filter. The filtrate is exited into a wastewater treatment station. 950 kg of wet cake is kept for later use.

D. Clarification treatment of gellan gum

The cake obtained in C is firstly dispersed by a beater into short fibers. And, deionized water in the amount of 15 times of the weight of the short fibers is added to form a solution. The solution is heated up to the temperature of 90° C. Into the solution, a suitable amount of diatomite is added and dispersed evenly with agitation. The temperature is controlled around 85° C. A chamber-type polypropylene plate-and-frame filter press having a precoating of the filter aid for diatomite is used to cyclically filter the gellan gum solution until the clarified gellan gum solution has a transmittancy of above 92%, measured with a spectrophotometer. The clarified solution is pumped into a gel tank.

E. Dehydration treatment of the deacetylated gellan gum solution

The temperature of the gellan gum solution obtained in D needs to be kept at a temperature of above 65° C. to prevent from the formation of gel. Then, 25 L of calcium chloride solution having a concentration of 30% and a slow agitation is conducted for 5 minutes. Then, the temperature is forcedly reduced to a temperature below 50° C. The colloid of the hard and brittle gel as formed is pressed with a chamber-type polypropylene plate-and-frame filter press. And 500 kg sheets or curds of gellan gum having a water content of about 80% are obtained.

F. Ion exchange and decoloration treatment

The gellan gum sheets or curds obtained in E are cut into column-shaped grains with a cutter. The diameter of the grains is less than 3 mm, and the length of the grains is less than 12 mm. The gellan gum grains are plunged into deionized water of the amount of 3 times of the gellan gum grains in mass. At the same time, potassium sulfate is added until the concentration of potassium sulfate reaches 8000 ppm, and a slow agitation is conducted for 10 minutes. Then, the solution is filtered with a filter cloth. The filter residue is immersed into an ethanol solution in the weight of 2.5 times of the filter residue, and a quick agitation is conducted for 30 minutes. The ethanol solution is removed with a sack press. Thereby, 495 kg of gellan gum product, in the form of wet and loose grains, is obtained.

G. Formulating a proper amount of chelating agent/acid system

Into the gellan gum obtained in F, 9.5 kg of potassium hexametaphosphate is added and 0.8 kg of malic acid added. The mixture is mixed evenly.

H. Drying and milling

The product obtained in G passes a vacuum drier and is dried at the temperature 75° C. The dried product is milled until 95% of it can pass a sieve of 80 meshes. 108 kg of low acyl and clarified gellan gum product is obtained.

In view of the existing post extraction process for preparing food-level low acyl gellan gum, the low acyl gellan suitable for use in the tissue culture medium produced using the above process has the following advantages:

1. The gellan gum has a good dispersivity. The hydration temperature is at about 60° C. At a lower temperature, it can dissolve and formulate into a gel having a very high transmittancy.

2. The gellan gum powder and metal salt(s) can be mixed and then dissolved, there is no difficulty occurred for dissolution and no phenomenon of producing a lot of milk-white flocculants.

3. The quality of product is largely improved and reaches the advance level in the world, including in the country and outside the country. The appearance of the product is good, the transmittancy of the product is high, and the gel strength of the product is high. In particular, the chromaticity of the product is above 83%, the transmittancy of the product is above 90%, and the gel strength of the product is in the range of 400~650 g/cm2.

What we claimed is:

1. A post extraction process for preparing low acyl gellan, comprising the following steps:

(1) Deacylation treatment of fermentation broth:

The temperature of the fermentation broth is raised to 80~90° C., and an antioxidant is added and a base is added to adjust the pH value to deacylate the gellan gum, after the deacylation treatment is completed, an acid is added to lower the pH value;

(2) Enzyme treatment of fermentation broth:

Into the fermentation broth of Step (1), different enzyme preparations are added to remove the insoluble impurities and bacterial debris from the fermentation broth as much as possible;

(3) Flocculation of fermentation broth:

Into the fermentation broth treated in Step (2) with enzymes, a water-soluble alkali metal is added to flocculate, and the pH value is adjusted to a basic condition; a solid-liquid separation is conducted to remove a large part of water and pigments from the fermentation broth so that the raw product of gellan gum is obtained;

(4) Clarification treatment of gellan gum:

The raw product of gellan gum obtained in Step (3) is clarified so that a clarified low acyl gellan gum solution is obtained;

(5) Dehydration treatment of the deacylated gellan gum solution:

Into the gellan gum deacylated and clarified solution obtained in Step (4), an alkali metal ion is added to form a gel and a solid-liquid separation is conducted;

(6) Removal of divalent or polyvalent cations and decoloration treatment

The gellan gum obtained in Step (5) is cut into grains, most of the divalent or polyvalent cations in the gellan gum are removed by ion exchange or chelating; and a slight drying is conducted by press, the slightly-dried gellan gum is further immersed with a lower alcohol and along with agitation; and the solution is filtered to reach the effect of complete removal of the colored substances;

(7) Drying and milling:

The solid materials of gellan gum obtained in Step (6) are dried and milled, so that a highly transparent, low acyl, and clarified gellan gum product is obtained.

2. The post extraction process for preparing low acyl gellan according to claim 1, wherein there is the following steps between Step (6) and Step (7):

(6') Formulating a proper amount of chelating agent/acid system:

Into the gellan gum obtained in Step (6), a proper amount of chelating agent/acid system is formulated to chelate the possibly added divalent cations added during the use of gellan gum, and to keep the pH value in a relatively-stable condition; and then all the materials are mixed evenly.

3. A post extraction process for preparing low acyl and clarified gellan gum, comprising the following steps:
   (1) Deacylation treatment of fermentation broth:
   The temperature of the fermentation broth is raised up to 80~90° C., and an antioxidant is added, and at the same time, a base is added to adjust the pH value to conduct the deacylation;
   (2) Enzyme treatment of fermentation broth:
   Into the fermentation broth in Step (1), different enzymes preparations are added to remove the insoluble impurities and bacterial debris as much as possible;
   (3) Flocculation of fermentation broth:
   Into the fermentation broth treated in Step (2) with enzymes, a water-soluble alkali metal is added to flocculate, then the pH value is adjusted into a basic condition, and a solid-liquid separation is conducted so that a large part of water and pigments are removed from the fermentation broth, thereby the raw gellan gum product is obtained;
   (4) Clarification treatment of gellan gum:
   The raw gellan gum product obtained in Step (3) is subjected to a clarification treatment and a clarified low acyl gellan gum solution is obtained;
   (5) Dehydration treatment of the deacylated gellan gum solution Into the gellan gum deacylated and clarified solution obtained in Step (4), an alkali metal ion is added to form a gel and a solid-liquid separation is conducted;
   (6) Chelating and decoloration treatment:
   The gellan gum obtained in Step (5) is cut into grains, most of the divalent or polyvalent cations of the gellan gum are removed via chelating, the gellan gum is slightly pressed to a slightly dried condition and is immersed with a lower alcohol along with agitation; and then a filtration is conducted to reach the effect of complete decoloration;
   (7) Drying and milling:
   The gellan gum obtained in Step (6) is pressed to dry and the solid materials are dried and milled, so that a high transparent, low acyl and clarified gellan gum product is obtained.

4. A post extraction process for preparing low acyl gellan suitable for use in a tissue culture medium, comprising the following steps:
   (1) Deacylation treatment of fermentation broth:
   The temperature of the fermentation broth is raised to 80~90° C., and an antioxidant is added, and at the same time, a based is added to adjust the pH value to deacylation;
   (2) Enzyme treatment of fermentation broth:
   Into the fermentation broth in Step (1), different enzymes preparations are added to remove the insoluble impurities and bacterial debris as much as possible;
   (3) Flocculation of fermentation broth:
   Into the fermentation broth treated in Step (2) by enzymes, a water-soluble alkali metal is added to flocculate, and the pH valued is adjusted into a basic condition; a solid-liquid separation is conducted to remove a large part of water and pigments from the fermentation broth; and thereby, the raw gellan gum product is obtained;
   (4) Clarification treatment of gellan gum:
   The gellan gum obtained in Step (3) is subjected to a clarification treatment and a clarified low acyl gellan gum solution is obtained;
   (5) Dehydration treatment of the deacylated gellan gum solution:
   Into the gellan gum deacylated and clarified solution obtained in Step (4), an alkali metal ion is added to form a gel and a solid-liquid separation is conducted;
   (6) Ion exchange and decoloration treatment:
   The gellan gum obtained in Step (5) is cut into grains, a large part of the divalent cations in the gellan gum is removed by ion exchange, the gellan gum obtained is slightly pressed and dried, and is immersed in a lower alcohol; an agitation is conducted; a filtration is performed to reach the effect of complete decoloration;
   (6') Formulating a proper amount of chelating agent/acid system:
   Into the gellan gum obtained in Step (6), a proper amount of chelating agent/acid system is added to chelate the additional divalent cations added during the use of gellan gum, and to stabilize the pH value in a relatively stable condition; and the materials are mixed evenly with an agitation;
   (7) Drying and milling:
   The solid material of gellan gum obtained in Step (6') is dried and milled, so that a highly transparent, low acyl and clarified gellan gum product is obtained.

5. The process according to claim 1, wherein, an acid is added to adjust the pH value to the neutral condition after the deacylation of Step (1), and the temperature is reduced to below 40° C.

6. The process according to any one of the preceding claims claim 1, wherein the antioxidant added in Step (1) is one or more of ascorbic acid, sodium erythorbate, sodium pyrosulfite, potassium pyrosulfite, potassium bisulfate and cysteine, and the concentration of the antioxidant is 100~300 ppm.

7. The process according to claim 6, wherein the concentration of the antioxidant is 150~250 ppm.

8. The process according to claim 1, wherein the base added in Step (1) for adjusting the pH is one or more of NaOH, KOH, Na2CO3, and K2CO3.

9. The process according to claim 8, wherein the base added in Step (1) for adjusting the pH is one or more of NaOH and KOH.

10. The process according to claim 8, wherein the base added in Step (1) for adjusting the pH is NaOH.

11. The process according to claim 1, wherein the base used in Step (1) adjusts the pH value to the range of 9.5~11.

12. The process according to claim 11, wherein the base used in Step (1) adjusts the pH value to about 10.

13. The process according to claim 1, wherein in Step (1), the base for adjusting pH is firstly formulated into a solution having the concentration of 10%.

14. The process according to claim 1, wherein in Step (1), the temperature is kept in the range of 85~90° C.

15. The process according to claim 13, wherein in Step (1), the temperature is kept in the range of 86~88° C.

16. The process according to claim 1, wherein in Step (1), the acid for adjusting the pH is an inorganic acid or an organic acid.

17. The process according to claim 16, wherein in Step (1), the acid for adjusting the pH is an inorganic acid.

18. The process according to claim 16, wherein the inorganic acid is one or more of hydrochloric acid, sulfuric acid or phosphoric acid.

19. The process according to claim 18, wherein the inorganic acid is hydrochloric acid.

20. The process according to claim 16, wherein the organic acid is one or more of formic acid, acetic acid, citric acid, malic acid, or tartaric acid.

21. The process according to claim 1, wherein in Step (1), the acid for adjusting the pH is used at an amount that makes the pH of the fermentation broth system adjusted to about pH 7.

22. The process according to claim 1, wherein in Step (1), the acid for adjusting the pH is firstly formulated into a solution having the concentration of 10%.

23. The process according to claim 1, wherein Step (2) is to add cellulase, lysozyme and protease, respectively, into the fermentation broth obtained in Step (1).

24. The process according to claim 23, wherein in Step (2), the enzyme and the condition are respectively: for cellulase, with the concentration being 500~2000 ppm, and the time being 4 to 8 hours, and the temperature being 40~50° C.; for lysozyme, with the concentration being 50~300 ppm, the time being 2 to 4 hours, and the temperature being 30~40° C.; and for neutral protease or alkaline protease, with the concentration being 100~1000 ppm, the time being 1 to 5 hours, and the temperature being 30~40° C.

25. The process according to claim 24, wherein for cellulase, the concentration being 1000~1500 ppm, the time being 5 to 6 hours, and the temperature being 43~45° C.; for lysozyme, the concentration being 100~200 ppm, the time being 2.5 to 3.5 hours, the temperature being 35~37° C.; and for neutral protease or alkaline protease, the concentration being 300~500 ppm, the time being 2 to 3 hours, and the temperature being 30~35° C.

26. The process according to claim 1, wherein Step (3) is to reduce the temperature of the material in Step (2) to a temperature below 35° C., add a divalent or polyvalent water-soluble alkali metal salt to flocculate the low acyl gellan gum, and then add a base to adjust the pH; and then a solid-liquid separation is conducted by either configuration or press.

27. The process according to claim 26, wherein the water-soluble alkali metal salt used in Step (3) includes a water-soluble salt of magnesium, calcium, barium, and zincum, or a combination of these salts.

28. The process according to claim 26, wherein the water-soluble alkali metal used in Step (3) is added at an amount that accounts for 0.1%~0.5% of the mass of the fermentation broth.

29. The process according to claim 28, wherein the water-soluble alkali metal used in Step (3) is added at an amount that accounts for 0.3%~0.4% of the mass of the fermentation broth.

30. The process according to claim 26, wherein the base used in Step (3) comprises KOH, NaOH, Na2CO3, NaHCO3, Na3PO4 or a combination thereof.

31. The process according to claim 1, wherein the device for the solid-liquid separation used in Step (3) is a chamber-type polypropylene plate-and-frame filter press or a sack press.

32. The process according to claim 31, wherein the device for the solid-liquid separation used in Step (3) is a chamber-type polypropylene plate-and-frame filter press.

33. The process according to claim 1, wherein Step (4) is to break up the material obtained in Step (3), and the broken fibers of gellan gum have a fiber length of not more than 10 cm, and the water content of the broken fibers is about 80%.

34. The process according to claim 33, wherein the broken fibers of gellan gum in Step (4) is dissolved with deionized water of the amount of 10 to 20 times of the broken fibers, and the solution so formed is heated to the temperature of 80~95° C.

35. The process according to claim 34, wherein the broken fibers of gellan gum in Step (4) is dissolved with deionized water of the amount of 15~20 times of the broken fibers, and the solution so formed is heated to the temperature of 85~90° C.

36. The process according to claim 1, wherein in Step (4), the clarification is conducted with a plate-and-frame filter press or a chamber-type filter press, high speed centrifugation, or a filtration with a microporous filter membrane.

37. The process according to claim 36, wherein the clarification step in Step (4) is conducted with a plate-and-frame filter press or a chamber-type filter press.

38. The process according to claim 1, wherein the temperature in the clarification treatment in Step (4) is above 65° C.

39. The process according to claim 38, wherein the treatment temperature is about 75° C.

40. The process according to claim 1, wherein the metal salt added in the formation of the gel in Step (5) includes a soluble monovalent alkali metal salt, a divalent alkali metal salt, a polyvalent alkali metal salt, or a combination thereof.

41. The process according to claim 40, wherein the monovalent alkali metal salt added for the formation of the gel is used at the amount of 0.8~1.2% (weight percent) of the clarified solution, and the divalent metal salt is used at the amount of 0.05~0.1% (weight percent) of the clarified solution.

42. The process according to claim 40, wherein the metal salt added for the formation of a gel in Step (5) is a monovalent and a divalent alkali metal salt.

43. The process according to claim 42, wherein the metal salt added for the formation of a gel in Step (5) is a divalent alkali metal salt.

44. The process according to claim 40, wherein the monovalent alkali metal salt is selected from the group consisting of one of potassium chloride, sodium chloride, potassium sulfate, sodium sulfate, or a combination thereof.

45. The process according to claim 40, wherein the divalent alkali metal salt is selected from the group consisting of one of calcium chloride and magnesium chloride, or a combination thereof.

46. The process according to claim 40, wherein the polyvalent alkali metal is ferric chloride.

47. The process according to claim 1, wherein in Step (5), the soluble metal salt added for the formation of gel is firstly formulated into a solution with the concentration of 30%.

48. The process according to claim 1, wherein the device for solid-liquid separation used in Step (5) is a chamber-type polypropylene plate-and-frame filter press or a sack press.

49. The process according to claim 48, wherein the device for solid-liquid separation is a chamber-type polypropylene plate-and-frame filter press.

50. The process according to claim 1, wherein in Step (5), after the solid-liquid separation, it produces sheets or curds of low acyl and clarified gellan gum having a water content of about 80%.

51. The process according to claim 50, wherein Step (6) is to cut the low acyl gellan gum having a water content of about 80% obtained in Step (5) into grains, to plunge the grains into water treated with a suitable monovalent alkali metal salt of the amount of 3~5 times of the mass of the grains to immerse and subjected to a high speed agitation, to convert the colloid from divalent cation form into monovalent cation form by ion exchange; the treated gellan gum solution is pressed to dehydrate, and then is immersed in a lower alcohol solution and dipped for a while and subjected to high speed agitation; then, a filtration is conducted to the effect of complete removal of pigments.

52. The process according to claim 50, wherein Step (6) is to cut the low acyl gellan gum having a water content of about 80% obtained in Step (5) into grains, to plunge the grains into water treated with a suitable chelating agent of the amount of 3~5 times of the mass of the grains to immerse and subjected to a high speed agitation, to remove a large part of the divalent or polyvalent cations from the colloid; the treated gellan gum solution is pressed to dehydrate, and then is immersed into a lower alcohol solution in the amount of 2 times of the mass of the pressed gellan gum, and dipped for a while and subjected to a high speed agitation; and then, a filtration is conducted to the effect of complete removal of pigments.

53. The process according to claim 1, wherein, in Step (6), the low acyl gellan gum is cut into grains with a cutter, and the diameter of the grains is less than 3 mm, and the length of the grains is less than 12 mm.

54. The process according to claim 51, wherein the monovalent metal cation used in Step (6) is a soluble monovalent alkali metal salt.

55. The process according to claim 54, wherein the soluble monovalent alkali metal salt is potassium chloride, sodium chloride, potassium sulfate or sodium sulfate.

56. The process according to claim 53, wherein the monovalent metal cation used in Step 6 is used in the solution at a concentration of 5000~10000 ppm.

57. The process according to claim 56, wherein the concentration is 6000~8000 ppm.

58. The process according to claim 52, wherein the chelating agent used in Step (6) is one or more of sodium citrate, tripotassium citrate, sodium hexametaphosphate, potassium hexametaphosphate, sodium pyrophosphate, or potassium tripolyphosphate.

59. The process according to claim 58, wherein the chelating agent is sodium citrate or sodium hexametaphosphate.

60. The process according to claim 1, wherein the chelating in Step (6) is used at the amount that the concentration in the solution is 1000~10000 ppm.

61. The process according to claim 60, wherein the amount of the chelating agent is 5000~8000 ppm.

62. The process according to claim 1, wherein the device for dehydration and press in Step (6) is a sack press.

63. The process according to claim 1, wherein the lower alcohol used in Step (6) is one or more of ethanol, isopropanol, and n-butanol.

64. The process according to claim 63, wherein the lower alcohol is ethanol or isopropanol.

65. The process according to claim 63, wherein the lower alcohol is isopropanol.

66. The process according to claim 1, wherein the amount of the lower alcohol used in Step (6) is 2~4 times of the weight of the wet grains of the gellan gum.

67. The process according to claim 66, wherein the amount of the lower alcohol is 2.5~3.5 times of the weight of the wet grains of the gellan gum.

68. The process according to claim 1, wherein the chelating agent used in Step (6') is one or more selected from the group consisting of sodium citrate, tripotassium citrate, sodium hexametaphosphate, potassium hexametaphosphate, sodium pyrophosphate, and potassium tripolyphosphate.

69. The process according to claim 1, the chelating used in Step (6') is the chelating agent: a salt of phosphoric acid.

70. The process according to claim 68, wherein the chelating agent is sodium hexametaphosphate.

71. The process according to claim 1, wherein the acid used in Step (6') is an inorganic acid or an organic acid.

72. The process according to claim 71, wherein the inorganic acid is one or more of hydrochloric acid, sulfuric acid or phosphoric acid.

73. The process according to claim 71, wherein the organic acid is one or more of formic acid, acetic acid, citric acid, malic acid, and tartaric acid.

74. The process according to claim 72, wherein the acid is an organic acid.

75. The process according to claim 74, wherein the organic acid is citric acid.

76. The process according to claim 1, wherein the amount of the chelating used in Step (6') accounts for 9~10% (mass percent) in the final dried product.

77. The process according to claim 1, wherein the amount of the acid used in Step (6') accounts for 0.5~1% (mass percent) in the final dried product.

78. The process according to claim 1, wherein Step (7) is to dry the product obtained in Step (6) or (6') at a temperature in the range of 75~80° C. and mill the dried product so that 95% of it passes a sieve of 80 meshes.

79. The process according to claim 1, wherein the drying device in Step (7) is a vacuum drier or a boiling drier, and the time for drying is in the range of 1 to 1.5 hours.

80. The low acyl gellan gum produced by the process according to claim 1.

* * * * *